US005601871A

United States Patent [19]
Krzysik et al.

[11] Patent Number: 5,601,871
[45] Date of Patent: Feb. 11, 1997

[54] SOFT TREATED UNCREPED THROUGHDRIED TISSUE

[76] Inventors: Duane G. Krzysik, 1112 E. Melrose Ave., Appleton, Wis. 54911; Theodore E. Farrington, Jr., 2121 Twin Willows Dr., Appleton, Wis. 54915; Lee P. Garvey, 113 Florida Ave., Little Chute, Wis. 54140; Cynthia W. Henderson, 411 Lowell Pl., Neenah, Wis. 54956; Robert D. Sauer, 8897 South Rd., Fremont, Wis. 54940; Michael J. Smith, 1124 Tullar Rd., Neenah, Wis. 54956; Michael C. Tuck, W2760 Brookhaven Dr., Appleton, Wis. 54915

[21] Appl. No.: 384,171

[22] Filed: Feb. 6, 1995

[51] Int. Cl.$^6$ ............................................. D21H 23/22
[52] U.S. Cl. .................. 427/288; 427/374.4; 427/398.1; 162/134; 162/135; 162/172; 162/173; 162/179
[58] Field of Search .................. 427/374.4, 280, 427/288, 398.1; 162/111, 112, 134, 135, 172, 173, 179, 136

[56] References Cited

U.S. PATENT DOCUMENTS

| | | | |
|---|---|---|---|
| 2,999,265 | 9/1961 | Duane et al. | 15/506 |
| 3,150,049 | 9/1964 | Emory | 167/90 |
| 3,264,188 | 8/1966 | Gresham | 167/84 |
| 3,619,280 | 11/1971 | Scheuer | 117/154 |
| 3,654,064 | 4/1972 | Laumann | 161/156 |
| 3,896,807 | 7/1975 | Buchalter | 128/261 |
| 3,950,578 | 4/1976 | Laumann | 427/378 |
| 4,063,754 | 12/1977 | Shackle et al. | 282/27.5 |
| 4,112,167 | 9/1978 | Dake et al. | 428/154 |
| 4,137,345 | 1/1979 | Falivene | 427/242 |

(List continued on next page.)

FOREIGN PATENT DOCUMENTS

| | | |
|---|---|---|
| 508516 | 5/1978 | Australia . |
| 564042 | 9/1983 | Australia . |
| 566215 | 10/1987 | Australia . |
| 579458 | 12/1987 | Australia . |
| 38925/89 | 7/1989 | Australia . |
| 620748 | 12/1990 | Australia . |
| 84845/91 | 9/1991 | Australia . |
| 638399 | 6/1993 | Australia . |
| 640529 | 8/1993 | Australia . |
| 644499 | 9/1993 | Australia . |
| 644457 | 12/1993 | Australia . |
| 0032793 | 3/1984 | European Pat. Off. . |
| 0165696 | 12/1985 | European Pat. Off. . |
| 0191128 | 8/1986 | European Pat. Off. . |
| 0257824 | 3/1988 | European Pat. Off. . |
| 0524892 | 1/1993 | European Pat. Off. . |
| 0631014 | 6/1994 | European Pat. Off. . |
| 631014 | 12/1994 | European Pat. Off. . |
| 2538238 | 8/1987 | France . |
| 2746098 | 4/1979 | Germany . |
| 8704537 U | 9/1987 | Germany . |
| 3720232 | 7/1988 | Germany . |
| 3924898 | 1/1991 | Germany . |
| 5916816 | of 1984 | Japan . |
| 62-236516 | of 1987 | Japan . |
| 63-275311 | of 1988 | Japan . |
| 2182999 | of 1990 | Japan . |
| 274694 | of 1990 | Japan . |
| 3182218 | of 1991 | Japan . |
| 415021 | of 1992 | Japan . |
| 520093 | of 1993 | Japan . |
| 1591294 | 6/1981 | United Kingdom . |
| WO9305752 | 4/1993 | WIPO . |
| WO9316678 | 9/1993 | WIPO . |
| WO9402674 | 2/1994 | WIPO . |

*Primary Examiner*—Michael Lusignan
*Assistant Examiner*—Erma Cameron

[57] ABSTRACT

A soft uncreped throughdried tissue product is disclosed having uniformly distributed surface deposits of a chemical composition which imparts a benefit to the user, such as a reduction in skin irritation during use. Particularly suitable compositions are those which have a melting point of from about 30° C. to about 70° C. and which are applied to the outer surfaces of the tissue product in melted form, preferably by rotogravure printing. A suitable composition contains an oil, a wax, and preferably a fatty alcohol.

24 Claims, 5 Drawing Sheets

U.S. PATENT DOCUMENTS

| | | | |
|---|---|---|---|
| 4,191,609 | 3/1980 | Trokhan | 162/113 |
| 4,481,243 | 11/1984 | Allen | 428/154 |
| 4,507,173 | 3/1985 | Klowak et al. | 162/112 |
| 4,513,051 | 4/1985 | Lavash | 428/212 |
| 4,550,035 | 10/1985 | Smith | 427/398.1 |
| 4,572,915 | 2/1986 | Crooks | 514/458 |
| 4,610,743 | 9/1986 | Salmeen et al. | 156/183 |
| 4,659,573 | 4/1987 | Frischling et al. | 424/63 |
| 4,735,935 | 4/1988 | McAnalley | 514/53 |
| 4,806,418 | 2/1989 | Sigl | 428/284 |
| 4,816,320 | 3/1989 | St. Cyr | 428/198 |
| 4,839,162 | 6/1989 | Komori et al. | 424/63 |
| 4,891,227 | 1/1990 | Thaman et al. | 424/443 |
| 4,891,228 | 1/1990 | Thaman et al. | 424/443 |
| 4,917,890 | 4/1990 | McAnalley | 424/195.1 |
| 4,950,545 | 8/1990 | Walter et al. | 428/446 |
| 5,048,589 | 9/1991 | Cook et al. | 162/109 |
| 5,085,856 | 2/1992 | Dunphy et al. | 424/64 |
| 5,129,988 | 7/1992 | Farrington et al. | 162/123 |
| 5,179,128 | 1/1993 | Lyle et al. | 252/165 |
| 5,281,306 | 1/1994 | Kakiuchi et al. | 162/158 |
| 5,348,620 | 9/1994 | Hermans et al. | 162/9 |
| 5,399,412 | 3/1995 | Sudall et al. | 428/153 |

SOFT TREATED UNCREPED THROUGHDRIED TISSUE

BACKGROUND OF THE INVENTION

Recently a process has been disclosed (European Patent Application Number 94109734.7, Pub. No. 0631014) which allows the production of soft absorbent tissue structures without the use of traditional Yankee dryer creping. Sheets produced by this uncreped throughdried process can be characterized as being very three dimensional with high bulk, high absorbent capacity and fast absorbent rate. However, because of the high degree of surface contour, such sheets can also abrade the skin. In addition, while the high absorbent capacity and fast absorbent rate of sheets produced in this manner can be ideal for some absorbent products, soft tissues such as facial and bathroom tissue often find advantages in a more controlled, even slow, absorbent rate while maintaining high absorbent capacity.

While it is known to provide tissues with lotions that can improve softness, the addition of such materials can decrease the thickness of the tissue sheets due to a partial collapse of the crepe structure when exposed to moisture and processing pressures. Thus, there is first a need to reduce the potential for skin abrasion while not losing the thickness of uncreped throughdried tissues. Secondly there is a need to better control absorbent rate without losing the high absorbent capacity of these sheets.

SUMMARY OF THE INVENTION

It has now been discovered that because of the wet resiliency of the uncreped throughdried basesheet, liquid treatment compositions can be applied to one or both outer surfaces of an uncreped throughdried tissue without substantially decreasing the absorbent capacity and the perceived thickness of the product. The liquid treatment composition can be water-based or oil-based. Suitable water-based compositions include, but are not limited to, emulsions and water-dispersible compositions which can contain, for example, debonders (cationic, anionic or non-ionic surfactants), or polyhydroxy compounds such as glycerine or propylene glycol. More typically, the uncreped throughdried basesheet would be treated with a bi-component system comprising a debonder and a polyhydroxy compound. Both components can be added separately or mixed together prior to being applied to the basesheet.

More specifically, a superior uncreped throughdried tissue can be made by uniformly applying, on the surface(s) of the tissue, large numbers of individual deposits of a melted moisturizing/protective composition comprising a wax and an oil, and thereafter resolidifying the composition to form a uniform distribution of solid deposits on the surface(s) of the tissue. Because the composition is a solid at room temperature and rapidly solidifies after deposition, it has less tendency to penetrate and migrate into the sheet. Compared to tissues with liquid formulations, this leaves a greater percentage of the added composition on the surface of the sheet where it can contact and transfer to the user's skin to provide a benefit. Furthermore, a lower add-on amount can be used to deliver the same benefit at lower cost because of the efficient placement of the composition substantially at the surface of the sheet.

Hence, in one aspect, the invention resides in a soft tissue product having one or more uncreped throughdried tissue plies, wherein a liquid composition has been added to one or both outer surfaces of the product without a substantial (20 percent or greater) decrease in the Absorbent Capacity and/or the perceived thickness of the product relative to the untreated tissue product.

In another aspect, the invention resides in an uncreped throughdried tissue product having one or more uncreped throughdried plies, wherein one or both of the outer surfaces of the product have distributed, preferably uniformly, solidified deposits of a composition comprising from about 30 to 90 weight percent oil and from about 10 to about 40 weight percent wax, preferably also containing from about 5 to about 40 weight percent fatty alcohol, said composition having a melting point of from about 30° C. to about 70° C., more specifically from about 40° C. to about 60° C. For purposes herein, "melting point" is the temperature at which the majority of the melting occurs, it being recognized that melting actually occurs over a range of temperatures.

In another aspect, the invention resides in a method of making a soft tissue product comprising (a) heating a composition comprising an oil, wax, and preferably a fatty alcohol, to a temperature above the melting point of the composition, causing the composition to melt, said composition having a melting point of from about 30° C. to about 70° C.; (b) uniformly applying the melted composition to one or both surfaces of a tissue web in spaced-apart deposits; and (c) resolidifying the deposits of the melted composition. Resolidification of the deposits can occur almost instantaneously, with out the need for external cooling means such as chill rolls, if the composition is heated to a temperature only slightly above or at the melting point of the composition. However, external cooling means such a chill rolls, either before or after the application of the melt, can be used if desired to accelerate resolidification. Such instantaneous resolidification tends to impede penetration of the composition into the tissue and retain it on the surface of the tissue, which is advantageous. For example, the temperature of the melted composition can advantageously be above the melting point about 100° C. or less, more specifically about 5° C. or less, and still more specifically about 2° C. or less. As the temperature of the melted composition approaches the melting point, the viscosity of the melted composition generally increases, which further enhances the tendency of the melted composition to be retained on the surface.

The amount of oil in the composition can be from about 30 to about 90 weight percent, more specifically from about 40 to about 70 weight percent, and still more specifically from about 45 to about 60 weight percent. Suitable oils include, but are not limited to, the following classes of oils: petroleum or mineral oils, such as mineral oil and petrolatum; animal oils, such as mink oil and lanolin oil; plant oils, such as aloe extract, sunflower oil, and avocado oil; and silicone oils, such as dimethicone and alkylmethyl silicones.

The amount of wax in the composition can be from about 10 to about 40 weight percent, more specifically from about 10 to about 30 weight percent, and still more specifically from about 15 to about 25 weight percent. Suitable waxes include, but are not limited to the following classes: natural waxes, such as beeswax and carnauba wax; petroleum waxes, such as paraffin and ceresine wax; silicone waxes, such as alkyl methyl siloxanes; or synthetic waxes, such as synthetic beeswax and synthetic sperm wax.

The amount of fatty alcohol in the composition, if present, can be from about 5 to about 40 weight percent, more specifically from about 10 to about 30 weight percent, and still more specifically from about 15 to about 25 weight percent. Suitable fatty alcohols include alcohols having a carbon chain length of $C_{14}$–$C_{30}$, including cetyl alcohol, stearyl alcohol, behenyl alcohol, and dodecyl alcohol.

In order to better enhance the benefits to consumers, additional ingredients can be used. The classes of ingredients and their corresponding benefits include, without limitation, $C_{10}$ or greater fatty alcohols (lubricity, body, opacity); fatty esters (lubricity, feel modification); vitamins (topical medicinal benefits); dimethicone (skin protection); powders (lubricity, oil absorption, skin protection); preservatives and antioxidants (product integrity); ethoxylated fatty alcohols; (wettability, process aids); fragrance (consumer appeal); lanolin derivatives (skin moisturization), colorants, optical brighteners, sunscreens, alpha hydroxy acids, natural herbal extracts, and the like.

The total tissue add-on amount of the composition can be from about 1 to about 40 weight percent, more specifically from about 5 to about 25 weight percent, and still more specifically from about 10 to about 15 weight percent, based on the weight of the tissue. The add-on amount will depend upon the desired effect of the composition on the product attributes and the specific composition. A preferred method to uniformly apply the heated composition to the surface of the tissue web is rotogravure printing, either direct or indirect (offset), because it is the most exact printing process and offers maximum control of the composition distribution and transfer rate. However, other printing methods, such as flexographic printing, can also be used.

The surface area coverage of the composition is preferably uniform over substantially all of the tissue surface, but only partially covers the surface(s) of the tissue product. This is achieved by a large number of small spaced-apart deposits which, when viewed by the naked eye, appear to cover the entire surface, but in fact do not. The actual surface area coverage of the deposits can be from about 30 to about 99 percent, more specifically from about 50 to about 80 percent. By providing a large number of very small deposits, the penetration of the composition can be more easily controlled to substantially remain on or near the surface of the tissue. Gravure printing is ideally suited to such an application by providing, for example, from about 10 to about 1000 deposits per lineal inch of surface, or from about 100 to about 1,000,000 deposits per square inch. This encompasses several well known engraving techniques, such as mechanical engraving, acid-etch engraving, electronic engraving and ceramic laser engraving. A suitable electronic engraved example is about 250 deposits per lineal inch of surface, or about 62,500 deposits per square inch. By providing such a large number of small deposits, the uniformity of the deposit distribution is very high. Also, because of the large number of small deposits applied to the surface of the tissue, the deposits more readily resolidify on the surface of the tissue where they are most effective in benefiting the user. As a consequence, a relatively low amount of the composition can be used to cover a large area.

The uniformity of the deposit distribution and the degree of penetration of the composition into the tissue can be quantified by image analysis of the surface or surfaces of the tissue after treatment with osmium tetroxide to stain the add-on composition black. The uniformity of the osmium-stained tissues can be characterized by a percent coefficient of variation of about 15 or less, more specifically about 10 or less, and still more specifically from about 5 to about 15. The degree of penetration (or lack of penetration) of the osmium-stained composition can be characterized by a mean gray level difference between opposite sides of the tissue, $GL_{DIFF}$ (hereinafter defined), of about 5 or greater, more specifically about 10 or greater, and still more specifically from about 5 to about 15.

The osmium tetroxide staining treatment used to measure the uniformity and the penetration of the composition is carried out by placing the tissues loosely in a glass bell jar having an opening diameter of about 12–16 inches and a depth of about 12 inches. Care is taken not to stack the tissues, which would hinder adequate penetration of the vapors to all tissues. Osmium tetroxide is received as a crystalline solid in a sealed glass ampule which is broken open and placed in the bell jar with the tissues. The top is placed on the bell jar forming an air-tight seal. The tissues remain in the bell jar for about 24 to 48 hours. The osmium tetroxide has a high vapor pressure and sublimes readily to a gas which permeates the bell jar chamber. After staining is complete, the bell jar is opened and the samples are allowed to ventilate 12 to 24 hours before handling in order to release any residual unreacted vapors. Note: The greatest care must be exercised when using osmium tetroxide. It is a powerful oxidizer and highly toxic. All procedures with this material should be conducted in a fume hood with adequate air flow.

In order to measure the percent coefficient of variation, the osmium-treated sheet is viewed with an omnidirectional darkfield lighting produced by an 8-bulb octagonal ring illuminator surrounding a 50 millimeter EL-Nikkor lens attached to a 10 millimeter C-mount extension tube. This is input into a Quantimet 970 Image Analysis System (Leica, Deerfield, Ill.) by a chainicon scanner. The field size (standard live frame) is 2.77 centimeters×2.17 centimeters. Various fields of the osmium-treated tissue sample are placed under the lens and measured using a black photodrape background. Six (6) fields in total are measured. The scanner white level is always set at 1.00 volt. At the end, the histogram is printed out and its standard deviation divided by its mean gray level is the coefficient of variation. When multiplied by 100, this becomes the percent coefficient of variation.

In order to determine the mean gray level difference, the imaging and optical conditions used are the same as described above for the uniformity measurement. But in this case, top surface and bottom surface pieces of each ply of tissue are placed tightly next to each other to form a "butt joint" with no gap between the two pieces. The sample is placed under the lens with, for example, the lighter bottom surface piece on the right of the image frame and the darker top surface piece on the left of the image frame.

If first measuring the gray-level histogram of the lighter, bottom surface, the variable live frame is placed over just that region of the image frame, with the scanner white level set at 1.00 volt for the whole field. Then the sample is rotated so that the lighter bottom surface is now on the left. The scanner is adjusted again to 1.00 volt and this surface is once again isolated by the variable live frame. This data is accumulated into the same gray-level histogram. The mean gray level of the bottom surface, $GL_{BOTTOM}$, is recorded.

The same procedure is then conducted on the darker, top surface that occupies the other half of the image, again with the scanner white level set at 1.00 volt for the entire image. (This will tend to compensate for the overall differences in the amount of the composition added to the tissue, while zeroing in more accurately on whether the composition is on the top or bottom surface, which reflects the degree of penetration.) Again, the mean gray level of the top surface, $GL_{TOP}$, is recorded.

Finally, the difference between the two mean gray levels, $GL_{DIFF}$, is calculated as a value inversely related to the penetration:

$$GL_{DIFF} = GL_{BOTTOM} - GL_{TOP}$$

Note that if $GL_{DIFF}$ is zero or negative, then complete penetration has occurred. If $GL_{DIFF}$ is strongly positive, then most of the osmium-stained composition is sitting on the top surface of the tissue.

In some embodiments, the products of this invention can be characterized by their hydrophobicity, which helps prevent "wet-through" to the user's hands during use. This property can be objectively measured by the Sink Time, which is described in U.S. Pat. No. 4,950,545 entitled "Multifunctional Facial Tissue" and issued Aug. 21, 1990 to Walter et al., which is herein incorporated by reference. The Sink Time can be about 30 seconds or greater, more specifically about 40 seconds or greater, still more specifically from about 50 to about 150 seconds or greater. These Sink Times can be dramatically increased by a factor of 3–5 times by heating the treated tissues of this invention to temperatures of from about 100 to about 150° F. Heat-treated tissues can exhibit Sink Times of about 150 or greater.

The tissue product of this invention can be one-ply, two-ply, three-ply or more. In all cases, the composition is applied to the outer surface(s) of the product. The composition can be applied after the plies are brought together or prior to bringing the plies together. The individual plies can be layered or blended (homogeneous). Surprisingly, it had been found that blended tissue basesheets provide equivalent performance to layered basesheets, hence layering is unnecessary.

DETAILED DESCRIPTION OF THE DRAWING

Figure 1:
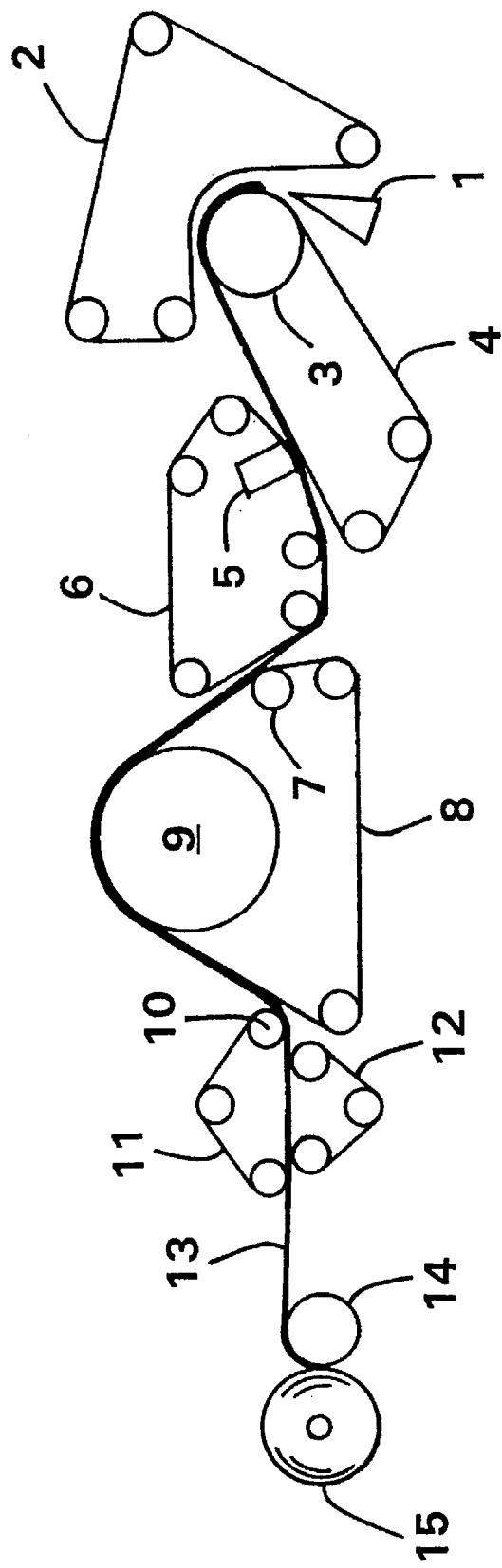
FIG. 1 is a schematic process flow diagram for a method of making an uncreped tissue base sheet as would be done in preparation for off-line printing of the heated composition.

Referring to FIG. 1, a method of carrying out this invention will be described in greater detail. FIG. 1 describes a process for making uncreped throughdried base sheets suitable for off-line application of the heated compositions. Shown is a twin wire former having a layered papermaking headbox 1 which injects or deposits a stream of an aqueous suspension of papermaking fibers onto the forming fabric 2. The web is then transferred to fabric 4, which serves to support and carry the newly-formed wet web downstream in the process as the web is partially dewatered to a consistency of about 10 dry weight percent. Additional dewatering of the wet web can be carried out, such as by vacuum suction, while the wet web is supported by the forming fabric.

The wet web is then transferred from the forming fabric to a transfer fabric 6 traveling at a slower speed than the forming fabric in order to impart increased MD stretch into the web. A kiss transfer is carried out to avoid compression of the wet web, preferably with the assistance of a vacuum shoe 5. The web is then transferred from the transfer fabric to the throughdrying fabric 8 with the aid of a vacuum transfer roll 7 or a vacuum transfer shoe. The throughdrying fabric can be traveling at about the same speed or a different speed relative to the transfer fabric. If desired, the throughdrying fabric can be run at a slower speed to further enhance MD stretch. Transfer is preferably carried out with vacuum assistance to ensure deformation of the sheet to conform to the throughdrying fabric, thus yielding desired bulk, flexibility, CD stretch and appearance.

The level of vacuum used for the web transfers can be from about 3 to about 15 inches of mercury (75 to about 380 millimeters of mercury), preferably about 10 inches (254 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the throughdrying fabric, the web is final dried to a consistency of about 94 percent or greater by the throughdryer 9 and thereafter transferred to an upper carrier fabric 11.

The dried basesheet 13 is transported between the upper and lower transfer fabrics, 11 and 12 respectively, to the reel 14 where it is wound into a roll 15 for subsequent printing of the heated composition and further converting.

Figure 2:
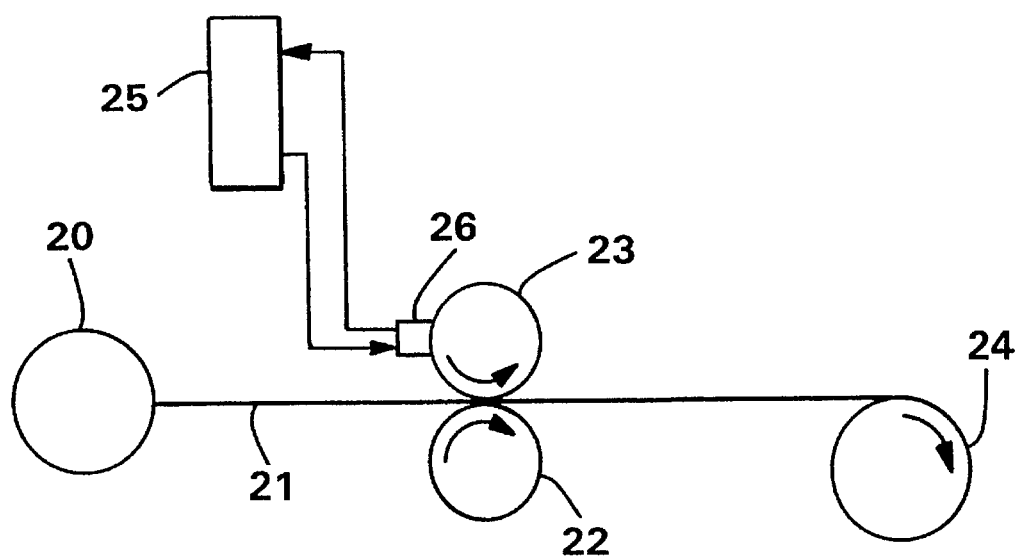
FIG. 2 is a schematic process flow diagram for a method of this invention in which parent rolls of uncreped throughdried tissue are treated on one side using an off-line heated gravure process.

FIG. 2 depicts off-line printing, in which the printing operation is carried out independently of the tissue sheet manufacturing process. The sheet being printed with the melted composition can be single ply or it can be multiple plies. Shown is a roll 20 of the tissue to be treated being unwound. The tissue sheet 21 is passed to a heated gravure printing station comprising a backing roll 22 and an engraved roll 23, at which point the treating composition is applied to one surface of the tissue. The resulting sheet is then wound into a roll 24 for further converting operations.

During the printing operation, the melted composition to be applied to the tissue sheet is supplied by a heated supply tank 25 and pumped to the heated doctor application head 26 by a suitable metering pump. It is necessary to maintain constant temperature in the process. Accordingly, the melted composition is continually circulated between the supply tank and the application head while maintaining an adequate amount in the reservoir. The heated doctor applicator head supplies the melted composition to the engraved roll 7, the surface of which contains a plurality of small cells having a transfer volume necessary to achieve the desired tactile effect. By way of example, a suitable engraved roll has a line screen of 250 and a volume of 5.0 billion cubic microns (BCM) per square inch of roll surface. Typical cell dimensions for this roll are 150 microns in length, 110 microns in width, and 30 microns in depth.

In operation the engraved roll is loaded to the backing roll 6 to force the tissue web or sheet into contact with the engraved roll. The backing roll can be any material that meets the process requirements such as natural rubber, synthetic rubber or other compressible surfaces. Loading pressures can vary from approximately 5–50 pli (roll to roll interference) to a gravure roll/backing roll gap of 0.008" (no roll to roll contact).

Figure 3:
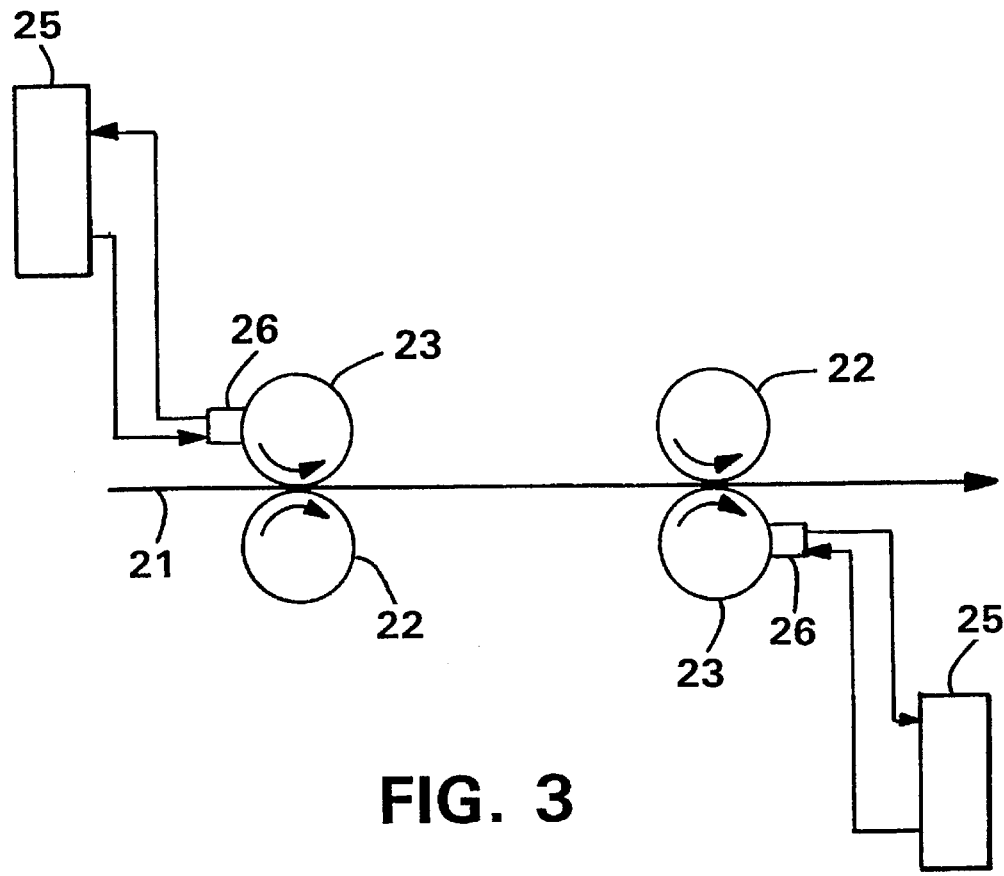
FIG. 3 is a schematic depiction of the heated rotogravure process in which the melted composition is applied to both sides of the tissue.

FIG. 3 is similar to FIG. 2, but illustrates two-sided direct heated rotogravure printing of the sheet using two printing stations in sequence. Two-sided printing is desirable when the effect of the composition is desired on both sides and/or the tissue sheet consists of two or more plies.

Figure 4:
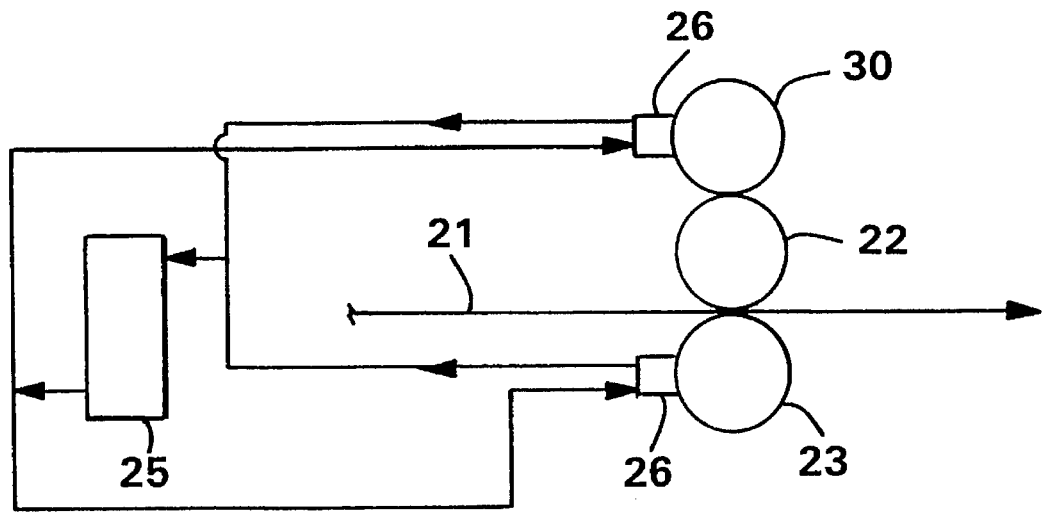
FIG. 4 is a further schematic depiction of a method of this invention in which both sides of the tissue product are printed with the melted composition using a combination of heated offset gravure printing and heated direct gravure printing.

FIG. 4 represents two-sided printing of the tissue sheet using an offset heated gravure printing method on one side of the sheet and a direct heated gravure printing method on the other side of the sheet. In this method, the engraved roll 23 and the backup roll 22 (now doubling as an offset applicator roll) can be the same as the rolls used for the previously described methods. However, the second engraved roll 30 requires different liquid delivery characteristics and thus is engraved slightly differently. For such rolls, for example, the direct engraving specifications can be 250 line screen, 5.0 BCM. Typical cell dimensions for such a roll can be 150 microns in length, 110 microns in width, and 30 microns in depth. The offset engraving specifications can be 250 line screen, 4.0 BCM, 140 microns in length, 110 microns in width, and 26 microns in depth.

Figure 5:
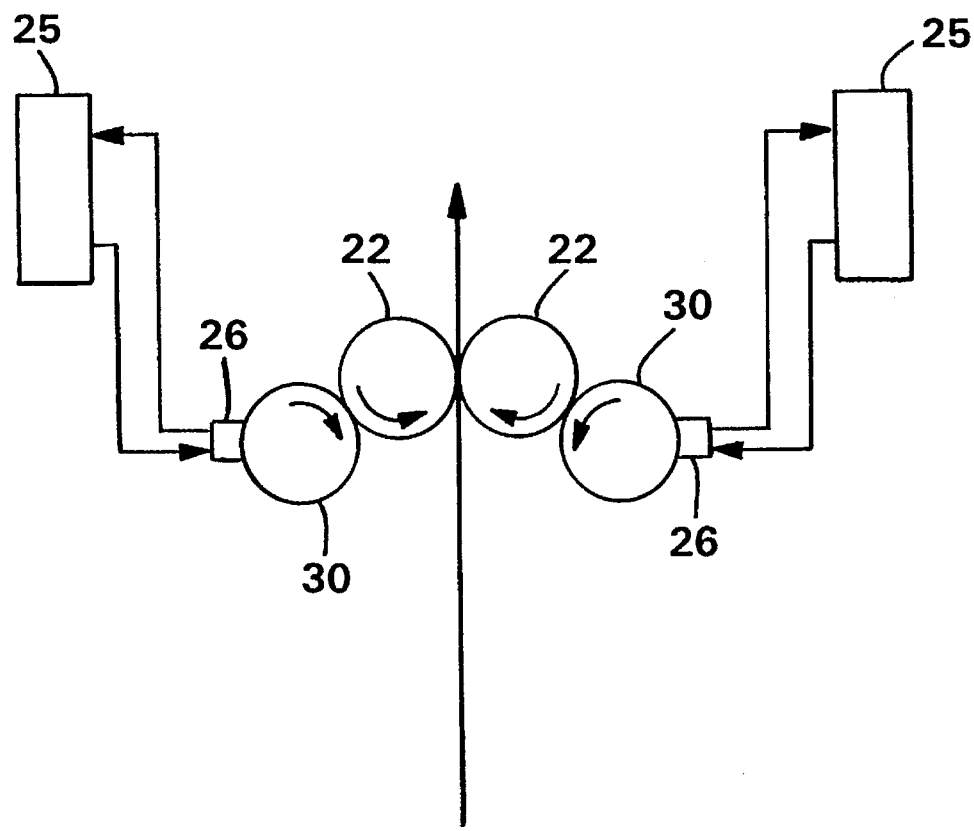
FIG. 5 is a further schematic depiction of a method of this invention in which both sides of a tissue are simultaneously printed with the melted composition using heated offset gravure printing.

FIG. 5 represents a method of printing both sides of the sheet using simultaneous heated offset gravure printing.

Figure 6:
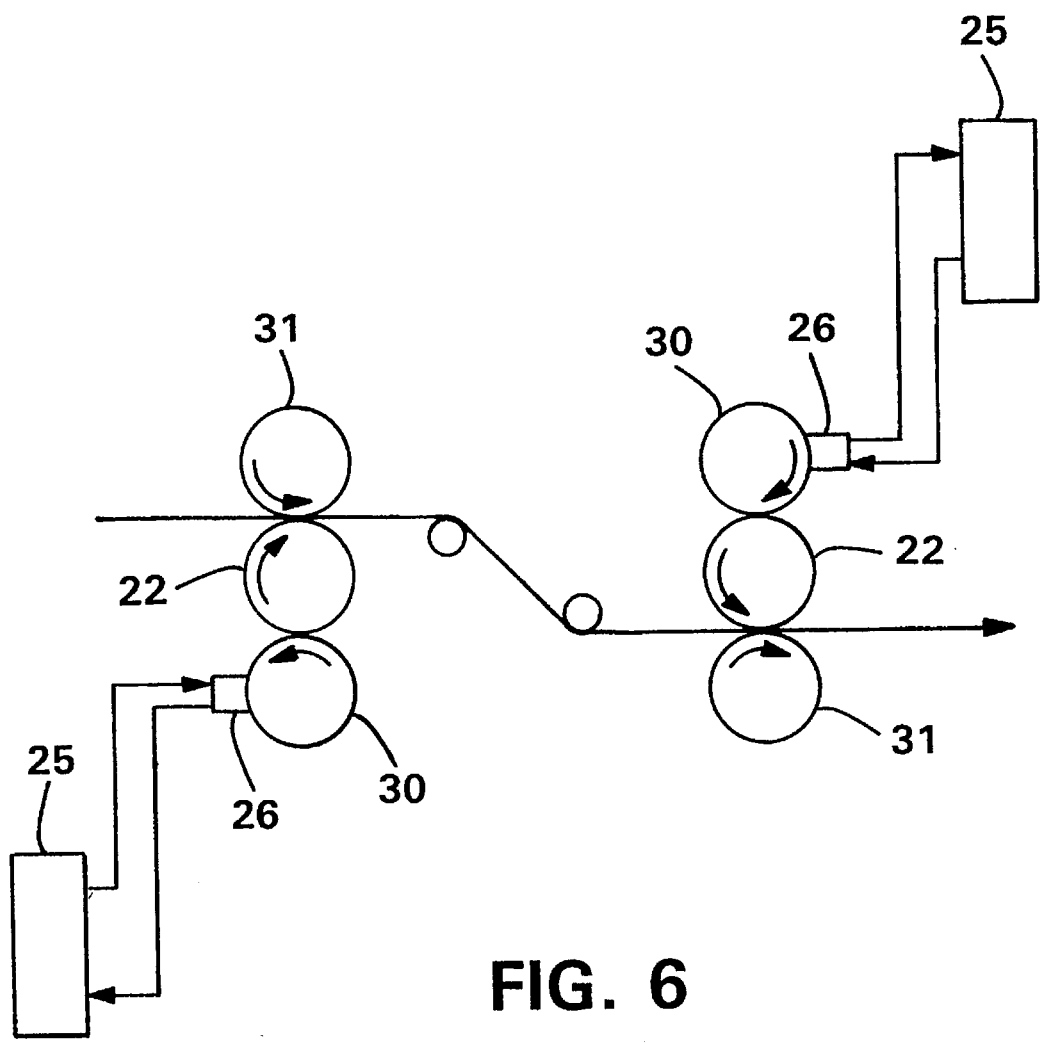
FIG. 6 is a further schematic depiction of a method of this invention in which both sides of the tissue sheet are consecutively printed with the melted composition using heated offset gravure printing.

FIG. 6 represents a method of printing both sides of the sheet in succession using two heated offset gravure printing stations. For each printing station, the addition of a backing roll 31 is necessary.

Figure 7:
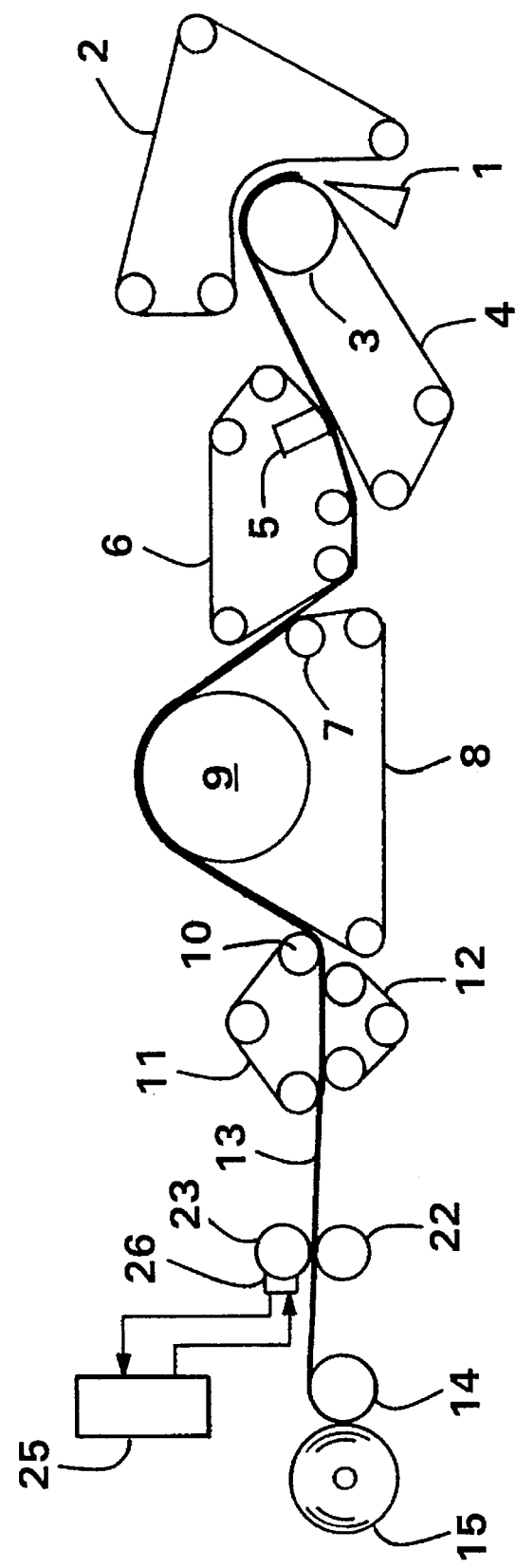
FIG. 7 is a schematic diagram showing a process for making an uncreped throughdried tissue sheet and applying the heated composition during the manufacturing process using a heated rotogravure printer in accordance with this invention.

FIG. 7 is similar to FIG. 1 except that the dried basesheet 13 is transported to a heated rotogravure printing station comprising backing roll 22 and engraved roll 23, at which point the melted composition is applied to one surface of the sheet. The treated uncreped throughdried tissue sheet is then wound into a roll 15 for subsequent converting operations.

EXAMPLES

Example 1

In order to further illustrate this invention, an uncreped throughdried tissue was produced using the method substantially as illustrated in FIG. 1. More specifically, three-layered single-ply bath tissue was made in which the outer layers comprised dispersed, debonded Cenibra eucalyptus fibers and the center layer comprised refined northern softwood kraft fibers.

Prior to formation, the eucalyptus fibers were pulped for 15 minutes at 10 percent consistency and dewatered to 30 percent consistency. The pulp was then fed to a Maule shaft disperser operated at 160° F. (70° C.) with a power input of 3.2 horsepower-days per ton (2.6 kilowatt-days per tonne). Subsequent to dispersing, a softening agent (Berocell 596) was added to the pulp in the amount of 15 pounds of Berocell per tonne of dry fiber (0.75 weight percent).

The softwood fibers were pulped for 30 minutes at 4 percent consistency and diluted to 3.2 percent consistency after pulping, while the dispersed, debonded eucalyptus fibers were diluted to 2 percent consistency. The overall layered sheet weight was split 35%/30%/35% among the dispersed eucalyptus/refined softwood/dispersed eucalyptus layers. The center layer was refined to levels required to achieve target strength values, while the outer layers provided the surface softness and bulk. Parez 631NC was added to the center layer at 10–13 pounds (4.5–5.9 kilograms) per tonne of pulp based on the center layer.

A four-layer headbox was used to form the wet web with the refined northern softwood kraft stock in the two center layers of the headbox to produce a single center layer for the three-layered product described. Turbulence-generating inserts recessed about 3 inches (75 millimeters) from the slice and layer dividers extending about 6 inches (150 millimeters) beyond the slice were employed. Flexible lip extensions extending about 6 inches (150 millimeters) beyond the slice were also used, as taught in U.S. Pat. No. 5,129,988 issued Jul. 14, 1992 to Farrington, Jr. entitled "Extended Flexible headbox Slice With Parallel Flexible Lip Extensions and Extended Internal Dividers", which is herein incorporated by reference. The net slice opening was about 0.9 inch (23 millimeters) and water flows in all four headbox layers were comparable. The consistency of the stock fed to the headbox was about 0.09 weight percent.

The resulting three-layered sheet was formed on a twin-wire, suction form roll, former with forming fabrics (12 and 13 in FIG. 1) being Lindsay 2164 and Asten 866 fabrics, respectively. The speed of the forming fabrics was 11.9 meters per second. The newly-formed web was then dewatered to a consistency of about 20–27 percent using vacuum suction from below the forming fabric before being transferred to the transfer fabric, which was traveling at 9.1 meters per second (30% rush transfer). The transfer fabric was an Appleton Wire 94M. A vacuum shoe pulling about 6–15 inches (150–380 millimeters) of mercury vacuum was used to transfer the web to the transfer fabric.

The web was then transferred to a throughdrying fabric (Lindsay Wire T216-3. The throughdrying fabric was traveling at a speed of about 9.1 meters per second. The web was carried over a Honeycomb throughdryer operating at a temperature of about 350° F. (175° C.) and dried to final dryness of about 94–98 percent consistency.

The resulting uncreped throughdried sheet had the following properties: basis weight, 17.0 pounds/2880 square feet; sensory panel Grittiness up (hereinafter defined), 4.59; sensory panel Grittiness down (hereinafter defined), 5.07; sensory panel Thickness (hereinafter defined), 4.62; Absorbent Rate (hereinafter defined), 1.9 seconds; and Absorbent Capacity (hereinafter defined), 10.8 grams of water per gram of fiber.

"Grittiness" is determined by a trained sensory panel tester, who places the sample of interest on a smooth surface and draws their middle and index fingers across the sample in all four directions. A numerical value of from 0–15 is assigned to the grittiest direction based on several standards for comparison. This is done for both sides of the tissue. "Grittiness Up" refers to the side of the sheet which was presented to the throughdrier fabric. "Grittiness Down" refers to the side of the sheet presented away from the throughdrier fabric. This parameter is associated with the amount of sharp or abrasive particles or fibers on the sheet surface. Higher numbers represent a higher degree of grittiness or abrasiveness.

"Thickness" is also determined by a trained sensory panel. It is representative of the perceived thickness as experienced by an ordinary tissue user. The Thickness is determined by holding the tissue with one's thumb between the index and second fingers. The sheet is then pulled out of this hold and a Thickness value of from 0–15 is assigned to the sample based on a comparison to several standard tissues of differing Thicknesses. Higher numbers mean greater perceived thickness. The "Absorbent Capacity" is determined by cutting 20 sheets of product to be tested into a 4 inches by 4 inches square and stapling the corners together to form a 20 sheet pad. The pad is placed into a wire mesh basket with the staple points down and lowered into a water bath (30° C.). When the pad is completely wetted, it is removed and allowed to drain for 30 seconds while in the wire basket. The weight of the water remaining in the pad after 30 seconds is the amount absorbed. This value is divided by the weight of the pad to determine the Absorbent Capacity, which for purposes herein is expressed as grams of water absorbed per gram of fiber.

The "Absorbent Rate" is determined by the same procedure as the Absorbent Capacity, except the size of the pad is 2.5 inches by 2.5 inches. The time taken for the pad to completely wet out after being lowered into the water bath is the Absorbent Rate, expressed in seconds. Higher numbers mean that the rate at which the water is absorbed is slower.

Example 2

Uncreped throughdried bath tissue was made as described in Example 1, except that a 50/50 blend of eucalyptus and southern hardwood was dispersed and used as a direct replacement for dispersed eucalyptus in the outer layers.

The resulting uncreped throughdried sheet had the following properties: basis weight, 17.0 pounds/2880 square feet; sensory panel Grittiness Up, 4.6; sensory panel Grittiness Down, 4.6; sensory panel Thickness, 4.9; Absorbent Rate, 1.8 seconds; and Absorbent Capacity, 10.8 grams of water per gram of fiber.

Example 3

Uncreped throughdried bath tissue was made as described in Example 2, except that a sheet basis weight of 16.0 pounds/2880 square feet was targeted.

The resulting uncreped throughdried sheet had the following properties: basis weight, 16.0 pounds/2880 square feet; sensory panel Grittiness Up, 5.6; sensory panel Grittiness Down, 5.9; sensory panel Thickness, 4.8; Absorbent Rate, 1.4 seconds; and Absorbent Capacity, 11.2 grams of water per gram of fiber.

Example 4

A skin-moisturizing formula having a melting point about 55°–60° C. was prepared having the following composition:

|  | Weight Percent |
| --- | --- |
| 1. Mineral Oil | 59.0 |
| 2. Ceresin Wax (M.P. 64–67° C.) | 20.0 |
| 3. Cetearyl Alcohol | 20.0 |
| 4. Zinc Oxide | 1.0 |

The formulation was prepared by heating the mineral oil to a temperature of 55°–60° C. The ceresin wax was added. The mixture was further heated to 60°–65° C., with agitation until the ceresin wax was melted. Cetearyl alcohol was slowly added to the mixture while maintaining agitation to avoid clumping. The temperature was maintained at about 55°–60° C. and mixing continued until the cetearyl alcohol was melted. The zinc oxide was added with continued mixing. At this point the formulation was ready for use.

The resulting formulation was applied to both surfaces of an uncreped throughdried tissue basesheet as described in Example 1 via a heated rotogravure printing process at an add-on level of 15 weight percent total add-on as described in FIG. 4. Specifically, the formulation was pre-melted at about 56° C. in a stainless steel heated supply tank. The press supply system and press (supply hoses, doctor application heads and gravure rolls) were pre-heated to about 55° C. The formulation was transferred from the heated application heads to the heated direct and offset gravure rolls.

The gravure rolls were electronically engraved, chrome over copper rolls supplied by Southern Graphic Systems, Louisville, Ky. The direct gravure roll had a line screen of 250 cells per lineal inch and a volume of 5.0 BCM per square inch of roll surface. Typical cell dimensions for this roll were 150 microns in length, 110 microns in width, and 30 microns in depth. The offset gravure roll was 250 line screen, 4.0 BCM, 150 microns in length, 110 microns in width and 26 microns in depth. The rubber backing roll/offset applicator roll was a 72 Shore A durometer Flex Touch 1 supplied by Republic Roller, Three Rivers, Mich.

The direct gravure roll was set up to a condition having about 0.003 inch clearance from the rubber backing roll. The offset gravure roll was set up to a condition having 0.375 inch interference between the gravure roll and the rubber backing roll. The combination heated direct and heated offset gravure printer was run at a speed of 50 feet per minute. The composition deposits solidified substantially instantaneously after exiting the press.

When converted into individual bath tissue rolls, the resulting tissue product was preferred by consumers for softness, thickness, absorbency and overall over CHARMIN® Plus bathroom tissue.

Examples 5–7

In order to illustrate the ability of compositions of this invention, in combination with an uncreped throughdried tissue sheet, to improve surface feel and reduce skin abrasion while not negatively impacting the perception of sheet thickness, and to control (slow) the absorbent rate while not significantly reducing absorbent capacity, three compositions as described in Table 1 below were prepared and applied to different uncreped throughdried tissue basesheets. The resulting properties of the treated tissue basesheets were compared to the untreated basesheet. All of the compositions had melting points in the range of from about 55° C. to about 60° C.

TABLE 1

|  | Heated Compositions | | |
| --- | --- | --- | --- |
| Ingredient | Composition 1 Weight Percent | Composition 2 Weight Percent | Composition 3 Weight Percent |
| Mineral Oil | 45 | 60 | 59 |
| Ceresin Wax | 20 | 20 | 19 |
| Behenyl Alcohol | 0 | 20 | 19 |
| Dimethicone | 2 | 0 | 0 |
| Isopropyl Palmitate | 4 | 0 | 0 |
| Acetulan | 5 | 0 | 0 |
| Aloe Vera Lipo Quinone | 2 | 0 | 0 |
| Vitamin E Acetate | 2 | 0 | 0 |
| Stearyl Alcohol | 20 | 0 | 0 |
| Zinc Oxide (Microfine) | 0 | 0 | 3 |

Example 5

The ability of Composition 2 to reduce the abrasiveness (Grittiness) of an uncreped throughdried tissue without significantly impacting the perception of thickness is demonstrated by Table 2. The uncreped throughdried tissue was produced as described in Example 1. The melted compositions were applied via off-line two-sided rotogravure printing as described in FIG. 4. The sample designated "Untreated" was run through the off-line machine but with the printing process inactive to achieve zero add-on. The higher add-on (15.6 weight percent) was achieved using the following machine conditions: The two-sided rotogravure process was operated with a 0.375 inch interference between the direct gravure roll and the rubber backing roll. The offset roll was set up to a condition having a 0.312 inch interference between the gravure roll and the backing roll (or offset applicator roll). The cell volumes of the direct and offset gravure rolls were 6.0 and 5.0 BCM, respectively. The printing process was heated and maintained at about 60° C. The decreased add-on (5.9 weight percent) was achieved by changing the 0.375 inch interference between the direct gravure roll and backing roll to 0.008 inch clearance. All of the other machine conditions remained the same. Note that the 5.9 and 15.6 weight percent add-ons had equal effect on sheet properties.

TABLE 2

Effect of Composition 2 on Sheet Grittiness and Thickness as Perceived by Human Sensory Panel

| Comp. | Add-on (wt % t) | Grittiness Up | Grittiness Down | Thickness |
| --- | --- | --- | --- | --- |
| Untreated | 0.0 | 2.04 | 2.28 | 4.15 |
| 2 | 5.9 | 1.67 | 1.68 | 4.30 |
| 2 | 15.6 | 1.6 | 1.78 | 4.23 |

Example 6

The ability of Compositions 1, 2 and 3 to affect large changes in absorbent rate without significantly decreasing absorbent capacity when applied to uncreped throughdried sheets is demonstrated in Table 3. The uncreped throughdried tissue was produced as described in Example 1. The heated formulations were applied via off-line two-sided rotogravure printing as described in Example 5.

TABLE 3

Effect of Compositions on Absorbent Rate and Absorbent Capacity

| Composition | Add-on (wt %) | Absorbent Rate(sec) | Absorbent Capacity |
| --- | --- | --- | --- |
| Base sheet | — | 1.8 | 10.8 |
| 1 | 16.4 | 13 | 9.4 |
| 2 | 15.4 | 190 | 9.8 |
| 3 | 14.9 | 103 | 9.8 |

As shown, the decrease in Absorbent Capacity was only about 10 percent, even though the Absorbent Rate was increased one or two orders of magnitude.

Example 7

The ability of Composition 2, at different add-on levels, to affect large changes in absorbent rate without significantly decreasing absorbent capacity when applied to uncreped throughdried sheets is demonstrated in Table 4 below. The base tissue sheet was produced as described in Example 1. The heated formulations were applied via off-line two-sided rotogravure printing as described in Example 5.

TABLE 4

Effect of Composition 2 on Absorbent Rate and Absorbent Capacity

| Composition | Add-on (wt %) | Absorbent Rate(sec) | Absorbent Capacity |
| --- | --- | --- | --- |
| Base sheet | — | 1.9 | 10.8 |
| 2 | 5.9 | 23.5 | 10.6 |
| 2 | 15.6 | 114 | 8.8 |

It will be appreciated that the foregoing examples, given for purposes of illustration, are not to be construed as limiting the scope of this invention, which is defined by the following claims and all equivalents thereto.

We claim:

1. A method of making a tissue product comprising:
   (a) heating a composition comprising an oil and a wax to a temperature above the melting point of the composition, causing said composition to melt, said composition having a melting point of from about 30° to about 70° C.;
   (b) applying from about 100 to about 1,000,000 deposits of the melted composition per square inch to one or both surfaces of an uncreped throughdried tissue web; and
   (c) resolidifying the deposits of the melted composition.

2. The method of claim 1 wherein the heated composition is applied to the tissue with a rotogravure printer.

3. The method of claim 2 wherein from about 30 to about 99 percent of the surface area of the tissue is covered with the composition.

4. The method of claim 2 wherein from about 50 to about 80 percent of the surface area of the tissue is covered with the composition.

5. The method of claim 1 wherein the amount of the composition applied to the tissue is from about 1 to about 40 weight percent based on the weight of the tissue.

6. The method of claim 1 wherein the amount of the composition applied to the tissue is from about 5 to about 25 weight percent based on the weight of the tissue.

7. The method of claim 1 wherein the amount of the composition applied to the tissue is from about 10 to about 15 weight percent based on the weight of the tissue.

8. The method of claim 1 wherein the tissue web is cooled before or after the deposits of the coating composition are applied in order to accelerate solidification of the deposits.

9. The method of claim 1 wherein the composition is heated to a temperature of about 10° C. or less above the melting point of the composition.

10. The method of claim 1 wherein the composition is heated to a temperature of about 5° C. or less above the melting point of the composition.

11. The method of claim 1 wherein the composition is heated to a temperature of about 2° C. above the melting point of the composition.

12. The method of claim 1 wherein the composition contains from about 5 to about 40 weight percent fatty alcohol.

13. The method of claim 12 wherein the fatty alcohol is cetyl alcohol.

14. The method of claim 12 wherein the fatty alcohol is stearyl alcohol.

15. The method of claim 12 wherein the fatty alcohol is behenyl alcohol.

16. The method of claim 12 wherein the fatty alcohol is dodecyl alcohol.

17. The method of claim 1 wherein the oil is petrolatum.

18. The method of claim 11 wherein the oil is mineral oil.

19. The method of claim 1 wherein the oil is a silicone oil.

20. The method of claim 1 wherein the wax is ceresin wax.

21. A method of making a tissue product comprising:
 (a) heating a composition comprising mineral oil and ceresin wax to a temperature above the melting point of the composition, causing the composition to melt, said composition having a melting point of from about 55° C. to about 60° C.;
 (b) applying from about 100 to about 1,000,000 deposits of the melted composition per square inch to one or both surfaces of an uncreped throughdried tissue web; and
 (c) resolidifying the deposits of the melted composition.

22. The method of claim 21 wherein the composition contains from about 5 to about 40 weight percent cetyl alcohol.

23. The method of claim 21 wherein the composition contains from about 5 to about 40 weight percent stearyl alcohol.

24. The method of claim 21 wherein the composition contains from about 5 to about 40 weight percent behenyl alcohol.

* * * * *